United States Patent [19]

Souryal

[11] Patent Number: 5,468,224
[45] Date of Patent: Nov. 21, 1995

[54] METHODS OF COLOR CODING INJECTABLE MEDICATIONS

[76] Inventor: Tarek O. Souryal, 7019 Hillcrest, Dallas, Tex. 75205

[21] Appl. No.: 376,687

[22] Filed: Jan. 23, 1995

Related U.S. Application Data

[63] Continuation of Ser. No. 159,681, Nov. 30, 1993, abandoned.

[51] Int. Cl.⁶ .................................................. A61M 31/00
[52] U.S. Cl. .............................................. 604/51; 604/56
[58] Field of Search .......................... 604/49–56, 403, 604/404, 416; 128/898; 424/7.1

[56] References Cited

U.S. PATENT DOCUMENTS

| | | | |
|---|---|---|---|
| 3,716,054 | 2/1973 | Porter et al. | 604/20 |
| 4,202,878 | 5/1980 | Ritze | 424/49 |
| 4,521,237 | 6/1985 | Logothetis | 65/42 |
| 4,585,435 | 4/1986 | Vaillancourt | 604/27 |
| 4,654,026 | 3/1987 | Underwood | 604/80 |
| 4,722,732 | 2/1988 | Martin | 604/132 |
| 4,795,429 | 1/1989 | Feldstein | 604/80 |
| 4,891,208 | 1/1990 | Janoff et al. | 424/1.1 |
| 5,114,004 | 5/1992 | Isono et al. | 206/222 |
| 5,130,230 | 7/1992 | Segall et al. | 435/1 |
| 5,224,674 | 7/1993 | Simons | 248/68.1 |
| 5,224,932 | 7/1993 | Lappas | 604/80 |
| 5,240,713 | 8/1993 | Ayer | 424/473 |
| 5,248,310 | 9/1993 | Barclay et al. | 604/891.1 |

OTHER PUBLICATIONS

Remington's Pharmaceutical Sciences, Gennaro, A. R., ed. (Mack Publishing Co., 1990), pp. 1288–1290.
Physician's Desk Reference (Medical Economics Company, Inc., 1992), p. 409.

*Primary Examiner*—C. Fred Rosenbaum
*Assistant Examiner*—Adam J. Cermak
*Attorney, Agent, or Firm*—William L. Clayborn; John M. Cone

[57] ABSTRACT

Injectable medications are color coded by adding harmless coloring materials to the medications themselves. In one embodiment of the invention, each medication is assigned a color. In another embodiment, a class of medications is assigned a color.

3 Claims, No Drawings

1

METHODS OF COLOR CODING INJECTABLE MEDICATIONS

This is a continuation of application Ser. No. 08/159,861, filed Nov. 30, 1993, now abandoned.

BACKGROUND OF THE INVENTION

The present invention is related to a uniform color coding system for distinguishing among injectable medications liquids. Those skilled in the art are aware that injectable medications include those that are administered intravenously and intramuscularly.

The problem of mistakenly administering one medication when another medication was intended has existed essentially since there were two possible medications. The consequences of confusing one medication with another can be disastrous. This is especially true for medications that are administered intravenously or intramuscularly due to the rapid onset of their actions.

Since virtually all injectable medications are colorless, the possibility of confusion is quite real and, in fact, occurs with alarming frequency. Nowhere is this risk of confusion greater than in an emergency setting. Emergency medical personnel are called upon to administer dangerous, even potentially deadly medications intravenously in often suboptimal settings such as crash sites, panicked emergency rooms, or even crowded sporting events. While the conditions under which emergency medical personnel operate perhaps present the greatest possibility of confusing medications, that possibility exists in virtually every situation in which a medication is being administered.

In the past, the problem of confusing medications has been approached from the outside by distinguishing the packaging of different medications from one another.

U.S. Pat. No. 1,032,610 (Kern) discloses a bottle having indications that it contains poison. In one embodiment, the bottle has external projections which provide a tactile indication that it contains poison. In another, the neck of the bottle contains a phosphorescent chemical which provides a visual indication that the bottle contains poison.

U.S. Pat. No. 3,826,222 (Romick) discloses a unit-dose medication handling system in which a dispensing container whose exterior surface has color coded sections.

U.S. Pat. No. 3,870,035 (Sarnoff) discloses a method and apparatus which allows a coronary prone individual to self-administer prehospital phase treatment shortly after the onset of heart attack symptoms. The disclosed apparatus includes colored lights, each of which correspond to a predetermined heartbeat rate range. Also provided are a plurality of medications in color coded injectors. The medication in each injector is that which is appropriate for treatment of the abnormal heart condition which corresponds to heartbeat range of the corresponding colored light.

U.S. Pat. No. 4,054,343 (Heyland) discloses a drug-dispensing apparatus in which a cassette dispenser is color coded to indicate the time at which a patient is to be given a medication.

U.S. Pat. No. 4,219,021 (Fink) discloses a multiposition stopcock valve having a color coded valve body and valve handle provide a visual indication of the identity of the medication flowing through the valve.

In order to improve safety and reduce the risk of inadvertent administration of potentially deadly medications, it is an object of the present invention to provide a uniform system of distinguishing between injectable medications. Color coding the medications themselves provides an indication of the drug being administered not only to the person administering the drug, but also to other medical personnel on the scene, thereby allowing the latter to double-check the former.

SUMMARY OF THE INVENTION

Injectable medications are color coded to enable medical personnel to distinguish between them. In one embodiment, such medications are color coded by particular medication. In another embodiment, such medications are color coded by class. In either embodiment, nonpharmacologically active materials are added to the medications to color them.

DETAILED DESCRIPTION

In a preferred embodiment of the invention, frequently used, potentially deadly injectable medications used by emergency medical personnel are color coded. For example, the following color coding system is for medications that are used quite frequently by emergency medical personnel:

| Medication | Color |
| --- | --- |
| lidocaine | red |
| epinephrine | blue |
| atropine | yellow |
| calcium | green |
| benadryl | orange |

In addition to the foregoing medications, other injectable medications are similarly color coded. Given that there are a finite number of readily distinguishable colors, those medications presenting the greatest danger to the patient if administered by mistake are given priority for color coding.

In an alternate embodiment of the invention, injectable medications are color coded by class of medication. For example:

| Type of Medication | Color |
| --- | --- |
| Heart stimulants | Red |
| Heart depressants | Blue |
| Antihistamines | Green |
| Blood clotters | Purple |
| Blood thinners | Yellow |
| Analgesics | Orange |

In either embodiment, the medications are colored by the addition of materials that are not pharmacologically active, such as methylene blue, sudan red, indigo carmine, and other harmless dyes.

It is preferable that either embodiment of the invention be applied uniformly. Such uniform application minimizes confusion among medical workers when moving from one facility or locale to another.

While the preferred embodiments of the invention have been described, it will be apparent to those skilled in this art that modifications may be made to the described embodiments without departing from the spirit of the present invention. For that reason, the scope of the invention is set forth in the following claims.

I claim:

1. A method for distinguishing a medication frequently used in emergency medicine and intended for injection through tile skin of a patient from other such medications, said method comprising the steps of:

(a) assigning a color to said medication;

(b) adding a suitably colored material to said medication; and (c) injecting tile combination resulting from steps (a) and (b) through the skin of a patient.

2. A method for distinguishing a class of medications intended for injection through the skin of a patient from other classes of such medications, wherein each class comprises a plurality of medications which cause a similar physiological effect, said method comprising the steps of:

a. assigning a color to said class of medications; and b. adding a suitably colored material to each medication in that class.

3. A method for distinguishing members of a class of medications intended for injection through the skin of a patient from members of other classes of such medications, wherein each class comprises a plurality of medications which cause a similar physiological effect, said method comprising the steps of:

a. assigning a color to said class of medications; and b. adding a suitably colored material to two or more members of said class of medications.

* * * * *

UNITED STATES PATENT AND TRADEMARK OFFICE
CERTIFICATE OF CORRECTION

PATENT NO. : 5,468,224
DATED : November 21, 1995
INVENTOR(S) : Tarek O. Souryal

It is certified that error appears in the above-indentified patent and that said Letters Patent is hereby corrected as shown below:

Column 3, lines 2 and 7, change "tile" to --the--.

Signed and Sealed this

Twenty-sixth Day of March, 1996

Attest:

BRUCE LEHMAN

Attesting Officer

Commissioner of Patents and Trademarks